United States Patent [19]

Sullivan

[11] Patent Number: 5,227,170
[45] Date of Patent: Jul. 13, 1993

[54] ENCAPSULATION PROCESS
[75] Inventor: Sean M. Sullivan, Pasadena, Calif.
[73] Assignee: Vestar, Inc., San Dimas, Calif.
[21] Appl. No.: 541,141
[22] Filed: Jun. 20, 1990

Related U.S. Application Data

[63] Continuation-in-part of Ser. No. 367,712, Jun. 22, 1989.
[51] Int. Cl.$^5$ ............................................. A61K 37/22
[52] U.S. Cl. ................................... 424/450; 424/417; 435/6
[58] Field of Search ................. 424/417, 450; 264/4.3, 264/4.1

[56] References Cited

U.S. PATENT DOCUMENTS

| | | | |
|---|---|---|---|
| 4,394,448 | 7/1983 | Szoka, Jr. et al. | 435/172 |
| 4,762,720 | 8/1988 | Jizomoto | 424/450 |

FOREIGN PATENT DOCUMENTS

| | | |
|---|---|---|
| 0290296 | 11/1988 | European Pat. Off. . |
| 01102 | 2/1986 | World Int. Prop. O. . |
| 89/04656 | 6/1989 | World Int. Prop. O. . |
| 90/07920 | 7/1990 | World Int. Prop. O. . |

OTHER PUBLICATIONS

Dyson, Cell Biology, Allyn and Bacon, Inc., Boston, (1974) pp. 296-303.
Budker et al. "Translocation of DNA Across Model Phospholipid Membranes. I. Mechanism of Translocation", Biol. Chem. (USSR) 4:55-66 (1987).
Budker et al. "Translocation of DNA Across Model Phospholipid Membranes. II. Factors Which Influence the Effectiveness of Translation" Biol. Chem. (USSR) 4:639-647 (1987).
Budker et al. "Translocation of DNA Across Model Phospholipid Membranes. III. Electron Microscope Analysis" Biol. Chem. (USSR) 4:1201-1207 (1987).
Szoka & Papahadjopoulos, Procedure for Preparation of Liposomes with Large Internal Aqueous Space and High Capture by Reverse-Phase Evaporation, Proc. Natl. Acad. Sci. USA, 75, 4194-4198 (1978).
Marc J. Ostro, Liposomes, Scientific American 256(1), 102-111 (Jan. 1987).
Paul G. Lurquin, Entrapment of Genetic Material into Liposomes and Delivery to Cells in Liposome Technology vol. II, Chapter 13. pp. 188-193, CRC Press, Boca Raton, Fla. (1984).
Felgner et al., Proc. Natl. Acad. Sci. USA 84, 7413-7417 (1987).
Wang & Huang, Biochem. Biophys. Res. Commun. 147, 980-985 (1987).
Mahler et al., Biol. Chem. 2nd Ed., Harper & Row, pp. 233-234 (1966).
Papahadjopoulos et al., Biochim. Biophys. Acta 394, 483-491 (1975).

Primary Examiner—Amelia Burgess Yarbrough
Attorney, Agent, or Firm—Adam Cochran; George Anthony Gilbert

[57] ABSTRACT

A process for the encapsulation of oligonucleotides in liposomes includes the suspending of liposomes containing a divalent cation in a solution containing an oligonucleotide and having an osmolarity of a less than that of the internal aqueous phase.

14 Claims, No Drawings

ENCAPSULATION PROCESS

BACKGROUND OF THE INVENTION

This is a continuation-in-part of application serial number 07/369,712 filed Jun. 22, 1989.

FIELD OF THE INVENTION

This invention relates to the fields of biochemistry and medicine, more particularly to the formation of stable liposome encapsulated oligonucleotides for use in vivo, and specifically to the encapsulation of oligonucleotides into pre-formed liposomes.

Liposomes are microscopic, spherical lipid vesicles which enclose an inner aqueous space. Liposomes are dispersed or suspended in an aqueous phase, and can be used to encapsulate and deliver pharmaceutical agents with greater safety and efficacy to specific body cells.

The walls of the vesicles are formed by at least one bimolecular layer of lipid components having polar (water-seeking) heads and non-polar (hydrophobic) tails, which are disposed so that the polar heads of the outer bilayer orient outwardly to extend into the surrounding aqueous medium, and the polar heads of the inner bilayer extend into the inner aqueous space of the liposome. The non-polar tails of the inner and outer layers then associate to form the bilayer membrane which defines the liposome. Unilamellar vesicles have one such bilayer, and multilamellar vesicles (MLVs) have a plurality of substantially concentric bilayers around the inner aqueous space, much like the lamellae of an onion, the bilayers being separated by interlamellar aqueous spaces between the facing polar heads.

DNA and RNA are unstable outside of a cell cytoplasm (particularly in serum), and accordingly methods for the in vivo use of these sequences for various therapeutic purposes has been inhibited. One method which has been proposed for the delivery of nucleotide sequences is liposomal encapsulation, which has been advantageously employed for other active agents. Liposomes can be targeted to various body cells and, if such sequences could successfully be encapsulated, liposome delivery of DNA would offer an opportunity to increase biological activity and expression of delivered genes.

Liposomal DNA encapsulation has been attempted, and has relied on passive oligonucleotide entrapment i.e., the encapsulation of oligonucleotides during liposome formation, e.g., forming liposomes by techniques such as reverse phase evaporation, dehydration/rehydration, or detergent dialysis from a lipid film dispersed in an aqueous phase containing DNA. These techniques have been used to encapsulate single and double stranded DNA from the size of a single gene to plasmid containing several genes, but inserting the oligonucleotide as the liposome is formed subjects the oligonucleotide to the considerable stresses of the post-formation manufacturing process, and presents problems associated with the lack of long term DNA/lipid stability. Moreover, serum stability sufficient for in vivo delivery of oligonucleotides requires the use of solid lipids, such as distearoylphosphatidylcholine (DSPC), distearoyl phosphatidylglycerol (DSPG) and cholesterol (CHOL), which have limited solubility in the solvents required in some passive entrapment processes.

As an example of another passive entrapment procedure, a publication by Papahadjopoulos, et al., *Biochim. Biophys. Acta* 394:483–491, 1975, discloses that phosphatidylserine (PS) liposomes fuse with one another in the presence of the divalent cations, $Ca^{+2}$ or $Mg^{+2}$, to form chocleate cylinders. Upon chelation of the divalent cation, the structures convert to large oligolamellar liposomes, and this phenomenon has been used to entrap DNA. Small unilamellar vesicles (SUVs) were formed from pure PS or PS in combination with phosphatidylcholine (PC) or PC/CHOL. Addition of $CaCl_2$ resulted in the formation of chocleate cylinders (unenclosed bilayers). The lipid was pelleted and DNA was added in water. Addition of a calcium chelator (EDTA) resulted in the chocleate cylinders re-forming into oligolamellar liposomes. The unentrapped DNA was removed, and the liposome encapsulated DNA was incubated with cells. The procedure requires the use of PS, which is chemically unstable, and the use of $Ca^{+2}$ limits this procedure to an in vitro research tool.

In the absence of liposomes, $Ca^{+2}$/DNA precipitation has been used as a standard transfection method. The precipitant is exposed to a high concentration of cells and the cells take up the precipitated DNA which either becomes integrated into the cellular DNA or exists as an episomal gene. The publications by Budker, et al., *Biological Membranes* (USSR) 4:55–66 (1987) and Budker, et al., *Biological Membranes* (USSR) 4:639–647 (1987) investigate the mechanism of this transfection procedure by substituting a large unilamellar liposome as a model for the cell membrane. The system has been characterized with respect to addressing the mechanism and optimal requirements for DNA encapsulation. The protocol consists of the addition of divalent cation to a DNA/lipid mixture under isosmotic (isotonic) conditions, i.e., under conditions in which the osmolarity of the solution in the internal aqueous spaces of the liposome is essentially isotonic with respect to the osmolarity of the external suspending solution. The addition of divalent cation triggers binding of the DNA to the liposome causing the lipid/DNA complex to be internalized. This results in a liposome within a liposome, and the DNA is in the inner liposome. The authors also report that causing the internal aqueous spaces to be hypertonic causes DNA to be released from the liposome.

While the in vivo delivery of liposomal nucleotide sequences offers significant opportunities for therapeutic treatment, such as the delivery of anti-sense DNA to cancer cells via tumor targeting liposomes or to HIV infected macrophage, problems such as the relative instability of the DNA/lipid combination and the wide variety of nucleotide sequences which may be therapeutically useful have made preformed liposomal nucleotide combinations impractical for intravenous use. It has thus been a desideratum to provide a method for the loading of nucleotides and nucleotide sequences into preformed liposomes which permits the loading of nucleotides after liposome formation, that is, an encapsulation method for nucleotide sequences that proceeds in the absence of passive encapsulation.

SUMMARY OF THE INVENTION

In contrast to the formation of liposomal oligonucleotides by the passive entrapment procedures described above, the present invention concerns the loading of nucleotides, nucleotide sequences, nucleotide analogues or derivatives into preformed liposomes. Preferably, the sequences are 500 nucleotides or less in length, and most preferably oligonucleotides of 5 to 150 nucleotides, and has shown particular advantages with respect to the encapsulation of single-stranded oligonucleotides. The term oligonucleotides, as used herein without qualifying language, means ribose or deoxyribose polymers of up to 500 nucleotides, i.e., up to 500 mer nucleotides. The liposomes may be of any type including MLVs or unilamellar vesicles (UVs), preferably include sufficient solid lipid to be stable in serum, and most preferably include cholesterol. Significant advantages have been obtained with liposomes which include both cholesterol and distearoylphosphatidylcholine.

A method for loading oligonucleotides into liposomes is provided, which comprises the steps of forming liposomes containing a divalent cation, the liposomes having an internal aqueous phase of a given osmolarity; and causing the loading of oligonucleotides into intact liposomes thus formed by suspending the liposomes in a solution containing an oligonucleotide and having an osmolarity of less than 50% that of the internal aqueous phase. The osmolarity of the external aqueous phase is preferably less than 25% of the osmolarity of the internal phase, and most preferably less than 10%. This method forms a dispersion including liposomes comprising an oligonucleotide and an ion selected from the group consisting of divalent cations contained in an internal aqueous phase of a given molarity within the liposomes, the liposomes being dispersed in a solution having an osmolarity of less than the amount of that of the internal aqueous phase. Preferably, the divalent cation is selected from the group consisting of calcium, manganese and magnesium; and most preferably is manganese.

DETAILED DESCRIPTION

Broadly, the method of the invention first involves the formation of liposome containing an aqueous solution of the divalent cation as the internal aqueous phase. This may be accomplished by a variety of known techniques, e.g., by dispersing appropriate lipids in an aqueous solution of the cation. Small unilamellar vesicles, smaller than $0.2\mu$, can be formed in a microemulsification apparatus and then sterile filtered to remove microorganisms if in vivo use is anticipated. Larger liposomes can be made under aseptic conditions according to the process of U.S. Pat. No. 4,935,171 or by other known means. Smaller liposomes can also be made from the larger multilamellar vesicles by extrusion or other known processes.

The liposomes thus formed are then separated from the cation solution, for example, by filtration or pelleting of the vesicles. A water solution of the nucleotide, having an osmolarity less than that of the internal aqueous phase as described above, is then added to the separated liposomes and the nucleotide is loaded into the internal phase. The loaded liposomes may then be further processed according to methods known in the art.

A preferred procedure involves liposome formation in the presence of 0.1M $MgCl_2$ by agitation. The volume of the external aqueous environment is decreased to reduce the quantity of external cation. A solution of an oligonucleotide in water is added to the preformed MLVs. The difference in osmotic pressure facilitates diffusion of the oligonucleotide across the liposomal membrane without completely disrupting, i.e., breaking, the MLVs. The method proceeds in the absence of a pH gradient such as is required in other loading procedures, and permits the loading of molecules of a significantly greater size.

The method of the invention permits the recovery of unencapsulated nucleotide sequences in the initial suspending solution, which can be used for subsequent loading procedures. The procedure yields 5% to 6% trapping efficiency. Even at an efficiency of 3% the remote loading of the invention permits cellular uptake of 100,000 DNA copies per cell.

Ribozyme entrapped by the method of the invention have been stable for one month at 4° C. and four months at −20° C. Stability in this regard refers to retention of oligonucleotide polymer length, which is analyzed by gel electrophoresis. The loading procedure has also been used to entrap a deoxyribose 8 mer which yielded $\approx 8\%$ entrapment and a 20 mer which yielded 5% entrapment. Smaller molecules have also been advantageously encapsulated such as deoxy adenosine triphosphate and calcein. All molecules were entrapped using DSPC/CHOL (2:1) liposomes. Calcein entrapment was also tested using dioleoylphosphatidylcholine (DOPC)/CHOL, dipalmitoylphosphatidylcholine (DPPC)/dimyristoylphosphatidylcholine (DMPC), DPPC/DMPC/DSPG, DOPC/CHOL/DLPG, and DSPC/CHOL/DSPG (57:33:10) liposomes. The DSPC/CHOL and DSPC/CHOL/DSPG liposomes gave similar trapping efficiencies, and this was at least 10-fold better than the other formulations. Substitution of 0.1M NaCl or 0.1M spermidine for $MgCl_2$ yielded 0.5% trapping efficiency.

This method for the entrapment of nucleotide sequences is performed in the absence of dehydration procedures, such as lyophilization, and thus facilitates loading immediately prior to use.

In the examples which follow, a variety of nucleotide sequences are entrapped in liposomes by the remote loading procedure of the invention. It should be understood that the word entrapment, when used with respect to the invention, refers to the enclosure of the nucleotides within the inner aqueous space (including the interlamellar regions of the bilayer) of the liposome. This is in contrast to the binding of the nucleotides to the outer surface of the liposomes, through charge or hydrogen binding, which may occur in other procedures. If the nucleotide is not thus entrapped within the liposome, significant dissociation or degradation will result in serum.

EXAMPLE 1

20 $\mu$mol of DSPC/CHOL (2:1) was prepared as a lipid film. The lipid film was vortexed into suspension using 0.1M $MgCl_2$ at 65° C. to form MLVs having an average diameter of one micron. This liposome suspension was frozen in liquid $N_2$ and thawed at 65° C. The freeze and thaw cycle was repeated three times to ensure that the salt was uniformly distributed throughout the lamellae. The osmolarity of the internal aqueous phase was 300 milliosmoles (mOsm). The liposome suspension was pelleted by centrifugation at 10K×g for 15 minutes to remove the external $MgCl_2$ solution. The supernatant was removed, and the liposome pellet was heated at 65° C. for 5 minutes. A solution of 17 mer DNA (20 $\mu$g in 100 $\mu$l $H_2O$, a solution having an osmolarity of $\approx 16$ mOsm) was preheated for 5 minutes at 65° C. and added to the liposome pellet. Heating at 65° C. was continued for 30 minutes. The sample was slowly cooled to room temperature and diluted with 1 ml PBS. Unentrapped DNA was removed by centrifugation of the MLVs followed by supernatant removal. The pellet was resuspended in fresh PBS and re-pelleted by centrifugation. This was repeated until no DNA was detected in the supernatant. The DNA was labeled at the 5' end with $^3$H- ATP. The phosphate backbone of the ribozyme was labeled with $^{32}$P. Trapping efficiency was determined by quantitating the amount of radioisotope associated with the pellet. The entrapped ribozyme were also analyzed by gel electrophoresis.

Additional examples were conducted by using the method set forth in the paragraph above with additional nucleotide sequences, including ATP, an 8 mer DNA, a methylphosphonate 8 mer, and a 37 mer single stranded RNA (ribozyme). The results are set forth in the following tables. Passively prepared antisense DNA/MLVs showed entrapment levels of $\leq 1\%$. The hypertonic loading procedure multiplied the entrapment 10 to 15 times and minimized surface-associated DNA with DSPC/CHOL (2/1).

TABLE ONE

MLV Encapsulation of 15 mer as a Function of Lipid Concentration

| LIPID CONCENTRATION | % ASSOCIATION | DNA/LIPID (mol/mol) |
|---|---|---|
| 10 mM (preformed) | 0.3 | $6.0 \times 10^{-7}$ |
| 10 mM | 0.5 | $1.0 \times 10^{-6}$ |
| 25 mM | 0.9 | $7.2 \times 10^{-7}$ |
| 50 mM | 1.2 | $4.8 \times 10^{-7}$ |
| 100 mM | 1.3 | $4.6 \times 10^{-7}$ |

TABLE TWO

| COUNTER ION | ILIGO-NUCLEOTIDE | % ENTRAPPED | % REMAINING[a] |
|---|---|---|---|
| $Mn^{+2}$ | 1.7 μg | 0.5 | 136.5 |
| $Mn^{+2}$ | 8.8 μg | 11.8 | 88.0 |
| $Mn^{+2}$ | 41.8 μg | 12.4 | 93.0 |
| $Mg^{+2}$ | 2.0 μg | 8.3 | 99.2 |
| $Mg^{+2}$ | 6.8 μg | 8.7 | 101.0 |
| $Mg^{+2}$ | 40.0 μg | 9.1 | 113.7 |

[a]Percent of initial entrapped amount remaining with liposome pellet after 79 hours.

TABLE FOUR

Effect of Encapsulated Counter Ion on Hypertonic Loading of 20mer Oligonucleotide and Stability of Entrapped Material[a]

| COUNTER ION | TRAPPING EFFICIENCY | % OF OLIGOMER ASSOCIATED LIPID AFTER 88 HRS[b] |
|---|---|---|
| $Ca^{+2}$ | 21.6 | 91.1 |
| $Mn^{+2}$ | 29.8 | 100.0 |
| $Zn^{+2}$ | 4.5 | 83.1 |
| $Fe^{+2}$ | 4.2 | 74.1 |
| $Mg^{+2}$ | 6.3 | 114.1 |
| $Cu^{+2}$ | 1.6 | 73.5 |

[a]Lipid-concentration, oligonucleotide concentration, hydration volume were kept constant and 0.1M counter ion was encapsulated.
[b]Lipid suspension was stored at 4° C. for 88 hours. Liposomes were pelleted and amount remaining with the lipid was divided by total DNA in the sample to determine value.

EXAMPLE 2

20 μmol of DPPG/DPPC/CHOL (50.1/16.9/33) was prepared as a lipid film. The lipid film was vortexed into suspension using 0.1M $MnCl_2$ (300 mOsm) at 65° C. to form MLVs having an average diameter of one micron. This liposome suspension was frozen in liquid $N_2$ and thawed at 65° C. The freeze and thaw cycle was repeated three times to ensure that the salt was uniformly distributed throughout the lamellae. The liposome suspension was pelleted by centrifugation at 10K ×g for 15 minutes. The supernatant was removed, and the liposome pellet was heated at 65° C. for 5 minutes. A solution of 142 mer RNA (150 μg in 100 μl $H_2O$, a solution having an osmolarity of $\approx 16$ mOsm) was preheated for 5 minutes at 65° C. and added to the liposome pellet. Heating at 65° C. was continued for 30 minutes. The sample was slowly cooled to room temperature and diluted to 0.4 ml PBS/EDTA (EDTA concentration was sufficient to chelate $Mn^{+2}$ and disaggregate the liposomes). The liposome/RNA suspension was extruded through a 0.4 μm, 0.2 μm polycarbonate filter to form UVs (unilamellar vesicles) of a diameter of less than 0.2 μm. Any SUV forming procedure which allows the use of high lipid concentration (i.e., the method described in U.S. Pat. No. 4,753,788) will provide at least comparable results. These liposomes were separated from unencapsulated RNA by gel filtration

TABLE THREE

Characterization of Hypertonic Loading of 17mer Oligonucleotides into Preformed MLVs

| | DNA/LIPID (mol/mol) | % ENCAPSULATION* |
|---|---|---|
| A. EFFECT OF TEMPERATURE | | |
| Hypertonic 25° C. | $1.3 \times 10^{-5}$ | 3.2 |
| Hypertonic 65° C. | $4.4 \times 10^{-5}$ | 6.0 |
| Isotonic 65° C. | $0.2 \times 10^{-5}$ | 0.5 |
| B. MONOVALENT VS. DIVALENT CATION | | |
| Hypertonic $Na^+$ | $0.2 \times 10^{-5}$ | 0.6 |
| Isotonic $Na^+$ | $0.3 \times 10^{-5}$ | 0.8 |
| Hypertonic $Mg^{+2}$ | $1.9 \times 10^{-5}$ | 4.8 |
| Isotonic $Mg^{+2}$ | $0.2 \times 10^{-6}$ | 0.6 |
| C. EFFECT OF LIPOSOME ENTRAPPED $Mg^{+2}$ CONCENTRATION | | |
| 0.00M | $0.2 \times 10^{-5}$ | 0.5 |
| 0.05M | $1.5 \times 10^{-5}$ | 3.7 |
| 0.10M | $1.9 \times 10^{-5}$ | 4.8 |
| 0.20M | $1.6 \times 10^{-5}$ | 4.0 |
| D. ENCAPSULATION OF OTHER OLIGONUCLEOTIDES BY PREFORMED MLVs CONTAINING 0.1M $MgCl_2$ | | |
| 8mer | $6.4 \times 10^{-5}$ | 8.9 |
| Methylphosphonate 8mer | $3.8 \times 10^{-5}$ | 5.3 |
| Ribozyme | $5.8 \times 10^{-5}$ | 2.4 |

*Encapsulation based upon amount entrapped divided by total amount of oligonucleotide added.

chromatography. The overall procedure yielded a trapping efficiency for the SUVs of 6%. Prior to extrusion, a 3% trapping efficiency was obtained. Trapping efficiency for the passive loading technique is about 0.5%.

The description above makes the advantages of the invention apparent to one of skill in the art. These advantages include the ability to form liposomal entrapped nucleotide sequences without the need for liposome forming procedures such as evaporation or lyophilization at the loading site, thus making possible the in vivo use of liposomal oligonucleotides. In addition, the oligonucleotides are completely internalized rather than binding to the outer surface of the liposomes (as shown by degradative enzyme criteria) resulting in serum stability. Further, the procedure of the invention has been shown to encapsulate single stranded oligonucleotides of from 5 to 142 nucleotides in length.

From this description the essential characteristics of the invention can be readily ascertained and, without departing from the spirit and scope thereof, the invention can be adapted to various usages. Changes in form and substitution of equivalents are contemplated as circumstances may suggest or render expedient, and although specific terms have been employed herein, they are intended in a descriptive sense and not for purposes of limitation.

I claim:

1. A method for loading nucleotides and nucleotide sequences into liposomes, comprising the steps of forming liposomes containing an ion selected from the group consisting of divalent cations in an internal aqueous phase, the internal aqueous phase being of a given osmolarity; and causing the loading of nucleotides into intact liposomes thus formed by suspending the liposomes in a solution containing a nucleotide or nucleotide sequence and having an osmolarity of less than 50% of that of the internal aqueous phase.

2. The method of claim 1 in which the cation is selected from the group consisting of calcium, manganese and magnesium.

3. The method of claim 1 or 2 in which the nucleotide is an oligonucleotide.

4. The method of claim 1 or 2 in which the osmolarity of the suspending solution is less than 25% of that of the internal aqueous phase.

5. The method of claim 3 in which the osmolarity of the suspending solution is less than 10% of that of the internal aqueous phase.

6. The method of claim 1 or 2 in which the osmolarity of the suspending solution is less than 10% of that of the internal aqueous phase.

7. The method of claim 3 in which the osmolarity of the suspending solution is less than 10% of that of the internal aqueous phase.

8. A dispersion comprising liposomes which include a nucleotide or nucleotide sequence and a divalent cation contained in an internal aqueous phase of a given osmolarity within the liposomes, the liposomes being dispersed in a solution having an osmolarity of less than 50% of that of the internal aqueous phase.

9. The dispersion of claim 8 in which the cation is selected from the group consisting of calcium, manganese and magnesium.

10. The dispersion of claim 8 or 9 in which the nucleotide is an oligonucleotide.

11. The dispersion of claim 8 or 9 in which the osmolarity of the suspending solution is less than 25% of that of the internal aqueous phase.

12. The dispersion of claim 10 in which the osmolarity of the suspending solution is less than 25% of that of the internal aqueous phase.

13. The dispersion of claim 8 or 9 in which the osmolarity of the suspending solution is less than 10% of that of the internal aqueous phase.

14. The dispersion of claim 10 in which the osmolarity of the suspending solution is less than 10% of that of the internal aqueous phase.

* * * * *

UNITED STATES PATENT AND TRADEMARK OFFICE
CERTIFICATE OF CORRECTION

PATENT NO. : 5,227,170
DATED : July 13, 1993
INVENTOR(S) : Sean M. Sullivan

It is certified that error appears in the above-indentified patent and that said Letters Patent is hereby corrected as shown below:

```
In the claims, at column 8, line 10, after the
word "than", please delete "10%" and replace with
--25%--
```

Signed and Sealed this

First Day of November, 1994

Attest:

BRUCE LEHMAN

Attesting Officer

Commissioner of Patents and Trademarks